(12) United States Patent
May et al.

(10) Patent No.: US 6,997,343 B2
(45) Date of Patent: Feb. 14, 2006

(54) SENSOR DISPENSING DEVICE

(75) Inventors: Stuart R. May, Chessington (GB);
David Brickwood, London (GB);
Graeme A. Maisey, Chessington (GB)

(73) Assignee: Hypoguard Limited, Woodbridge (GB)

( * ) Notice: Subject to any disclaimer, the term of this patent is extended or adjusted under 35 U.S.C. 154(b) by 520 days.

(21) Appl. No.: 10/233,265

(22) Filed: Aug. 30, 2002

(65) Prior Publication Data

US 2003/0089730 A1   May 15, 2003

Related U.S. Application Data

(60) Provisional application No. 60/336,921, filed on Dec. 3, 2001.

(30) Foreign Application Priority Data

Nov. 14, 2001  (GB)  .................................... 0127322

(51) Int. Cl.
B65H 1/08 (2006.01)
(52) U.S. Cl. ...................................... 221/232; 221/268
(58) Field of Classification Search ................ 221/232, 221/268
See application file for complete search history.

(56) References Cited

U.S. PATENT DOCUMENTS

| | | | |
|---|---|---|---|
| 3,836,033 A | 9/1974 | Mindt et al. |
| 3,838,033 A | 9/1974 | Mindt et al |
| 3,979,274 A | 9/1976 | Newman |
| 3,992,158 A | 11/1976 | Przybylowicz et al. |
| 3,993,451 A | 11/1976 | Verbeck |
| 4,053,381 A | 10/1977 | Hamblen et al. |
| 4,137,495 A | 1/1979 | Brown |
| 4,142,863 A | 3/1979 | Covington et al. |
| 4,216,245 A | 8/1980 | Johnson |
| 4,225,410 A | 9/1980 | Pace |
| 4,233,029 A | 11/1980 | Columbus |
| 4,273,639 A | 6/1981 | Gottermeier |
| 4,301,412 A | 11/1981 | Hill et al. |
| 4,301,414 A | 11/1981 | Hill et al. |
| 4,303,887 A | 12/1981 | Hill et al. |
| 4,312,834 A | 1/1982 | Vogel et al. |
| 4,413,407 A | 11/1983 | Columbus |
| 4,418,148 A | 11/1983 | Oberhardt |
| 4,473,457 A | 9/1984 | Columbus |
| 4,476,149 A | 10/1984 | Poppe et al. |
| 4,490,216 A | 12/1984 | McConnell |
| 4,502,938 A | 3/1985 | Covington et al. |
| 4,545,382 A | 10/1985 | Higgins et al. |
| 4,591,550 A | 5/1986 | Hafeman et al. |

(Continued)

FOREIGN PATENT DOCUMENTS

DE          19639226 A1     9/1996

(Continued)

OTHER PUBLICATIONS

Karl Schugerl et al., "Online-ProzeBanalyse In Bioreaktoren", No. 9, Germany, Sep., 1987.

(Continued)

*Primary Examiner*—Kenneth Noland
(74) *Attorney, Agent, or Firm*—O'Keefe, Egan & Peterman, LLP

(57) ABSTRACT

An embodiment of a sensor dispensing device for dispensing sensors for measuring analyte concentration in a fluid includes a cartridge assembly (32) having a housing (70) with an opening and means (16) for making a moisture-proof seal around the opening. A stack of sensors (12) is stored in the housing (70) and urged through the opening towards a stop member (73) by spring means. The device is provided with an externally actuable pusher (18) for breaking the seal and for pushing a single sensor from the housing.

6 Claims, 15 Drawing Sheets

U.S. PATENT DOCUMENTS

| | | | |
|---|---|---|---|
| 4,637,978 A | 1/1987 | Dappen | |
| 4,654,127 A | 3/1987 | Baker et al. | |
| 4,654,197 A | 3/1987 | Lilja et al. | |
| 4,713,327 A | 12/1987 | Findlay et al. | |
| 4,714,874 A | 12/1987 | Morris et al. | |
| 4,849,623 A | 7/1989 | Osaki et al. | |
| 4,897,173 A | 1/1990 | Nankai et al. | |
| 4,900,405 A | 2/1990 | Otagawa et al. | |
| 4,970,145 A | 11/1990 | Bennetto et al. | |
| 4,978,503 A | 12/1990 | Shanks et al. | |
| 5,108,564 A | 4/1992 | Szuminsky et al. | |
| 5,118,404 A | 6/1992 | Saito | |
| 5,120,420 A | 6/1992 | Nankai et al. | |
| 5,128,015 A | 7/1992 | Szuminsky et al. | |
| 5,141,868 A | 8/1992 | Shanks et al. | |
| 5,160,278 A | 11/1992 | Johnson | |
| 5,160,418 A | 11/1992 | Mullen | |
| 5,185,256 A | 2/1993 | Nankai et al. | |
| 5,228,972 A | 7/1993 | Osaka et al. | |
| 5,231,028 A | 7/1993 | Mullen | |
| 5,232,668 A | 8/1993 | Grant et al. | |
| 5,271,896 A | 12/1993 | Jakubowicz et al. | |
| 5,281,395 A | 1/1994 | Markart et al. | |
| 5,288,636 A | 2/1994 | Pollmann et al. | |
| 5,335,816 A * | 8/1994 | Kaufman et al. | 221/13 |
| 5,335,822 A * | 8/1994 | Kasper | 221/259 |
| 5,366,609 A | 11/1994 | White et al. | |
| 5,395,504 A | 3/1995 | Saurer et al. | |
| 5,407,554 A | 4/1995 | Saurer | |
| 5,413,690 A | 5/1995 | Kost et al. | |
| 5,429,735 A | 7/1995 | Johnson et al. | |
| 5,508,171 A * | 4/1996 | Walling et al. | 205/777.5 |
| 5,509,410 A | 4/1996 | Hill et al. | |
| 5,525,297 A | 6/1996 | Dinger et al. | |
| 5,526,120 A | 6/1996 | Jina et al. | |
| 5,628,890 A | 5/1997 | Carter et al. | |
| 5,660,791 A | 8/1997 | Brenneman et al. | |
| 5,682,884 A | 11/1997 | Hill et al. | |
| 5,708,247 A | 1/1998 | McAleer et al. | |
| 5,727,548 A | 3/1998 | Hill et al. | |
| 5,759,010 A | 6/1998 | Jacobs et al. | |
| 5,770,028 A | 6/1998 | Maley et al. | |
| 5,797,693 A | 8/1998 | Jaeger | |
| 5,820,551 A | 10/1998 | Hill et al. | |
| 5,985,116 A | 11/1999 | Ikeda et al. | |
| 5,989,917 A | 11/1999 | McAleer et al. | |
| 6,042,751 A | 3/2000 | Chan et al. | |
| 6,168,957 B1 | 1/2001 | Matzinger et al. | |
| 6,241,862 B1 | 6/2001 | McAleer et al. | |
| 6,248,596 B1 | 6/2001 | Durst et al. | |
| 6,258,229 B1 | 7/2001 | Winarata et al. | |
| 6,287,451 B1 | 9/2001 | Winarata et al. | |
| 6,338,790 B1 | 1/2002 | Feldman et al. | |
| 6,436,256 B1 | 8/2002 | Williams et al. | |
| 6,541,216 B1 | 4/2003 | Wilsey et al. | |
| 2002/0057993 A1 | 5/2002 | Maisey et al. | |
| 2002/0146835 A1 | 10/2002 | Modzelewski et al. | |
| 2003/0116583 A1 * | 6/2003 | Pugh | 221/268 |
| 2005/0150762 A1 | 7/2005 | Butters et al. | |
| 2005/0150763 A1 | 7/2005 | Butters et al. | |

FOREIGN PATENT DOCUMENTS

| | | |
|---|---|---|
| EP | 0010456 A1 | 4/1980 |
| EP | 0016387 A1 | 10/1980 |
| EP | 0034049 A1 | 8/1981 |
| EP | 0057110 A2 | 8/1982 |
| EP | 0078636 A1 | 5/1983 |
| EP | 0095946 A1 | 12/1983 |
| EP | 0096095 A1 | 12/1983 |
| EP | 0121385 A1 | 10/1984 |
| EP | 0127958 | 12/1984 |
| EP | 0136362 A1 | 4/1985 |
| EP | 0170375 B1 | 2/1986 |
| EP | 0171148 A1 | 2/1986 |
| EP | 0186286 A1 | 7/1986 |
| EP | 0200539 B1 | 11/1986 |
| EP | 0212314 A2 | 3/1987 |
| EP | 0215446 A2 | 3/1987 |
| EP | 0225061 A1 | 6/1987 |
| EP | 0230472 A1 | 8/1987 |
| EP | 0239222 A1 | 9/1987 |
| EP | 0255291 A1 | 2/1988 |
| EP | 0267724 A1 | 5/1988 |
| EP | 0271102 A2 | 6/1988 |
| EP | 0359831 A1 | 3/1990 |
| EP | 0170375 B1 | 5/1990 |
| EP | 0373413 A1 | 6/1990 |
| EP | 375363 A2 | 6/1990 |
| EP | 0115873 B1 | 11/1990 |
| EP | 0471986 A2 | 2/1992 |
| EP | 0127958 B1 | 3/1992 |
| EP | 0593096 A2 | 4/1994 |
| EP | 0636879 A2 | 2/1995 |
| EP | 0645627 A1 | 3/1995 |
| EP | 0732590 A3 | 1/1996 |
| EP | 0738666 B1 | 4/1996 |
| EP | 0732590 A2 | 9/1996 |
| EP | 0738666 A2 | 10/1996 |
| EP | 0771867 A2 | 5/1997 |
| EP | 0811843 A2 | 6/1997 |
| EP | 0885591 A2 | 12/1998 |
| EP | 0969097 A2 | 7/1999 |
| GB | 1318815 | 5/1973 |
| GB | 2001443 A | 1/1979 |
| GB | 2090659 A | 7/1982 |
| GB | 2227010 A | 7/1990 |
| GB | 2307231 A | 5/1997 |
| GB | 2337122 A | 11/1999 |
| GB | 2351153 A | 12/2000 |
| JP | 56163447 A | 12/1981 |
| JP | 59-40145 | 3/1984 |
| JP | 62030962 A | 2/1987 |
| JP | 62-237348 | 10/1987 |
| JP | 63-3248 | 1/1988 |
| JP | S61-146392 | 1/1988 |
| JP | 63-58149 | 3/1988 |
| JP | 63-137559 | 6/1988 |
| JP | 63-144245 | 6/1988 |
| JP | 63-144246 | 6/1988 |
| JP | 63-144247 | 6/1988 |
| JP | 63-317096 | 12/1988 |
| JP | 64-23152 | 1/1989 |
| JP | 64-23153 | 1/1989 |
| JP | 64-23154 | 1/1989 |
| JP | 1-14746 | 5/1989 |
| JP | 1-114747 | 5/1989 |
| JP | 1-134242 | 5/1989 |
| JP | 1-134243 | 5/1989 |
| JP | 1-134244 | 5/1989 |
| JP | 1-212345 | 8/1989 |
| JP | 1-253648 | 10/1989 |
| JP | 1-291153 | 11/1989 |
| JP | 2-62952 | 3/1990 |
| JP | 11344460 A | 12/1999 |
| WO | WO 88/03270 | 5/1988 |
| WO | WO 89/08713 | 9/1989 |
| WO | WO 92/14836 | 9/1992 |
| WO | WO9215861 A1 | 9/1992 |
| WO | WO94/10558 | 11/1993 |
| WO | WO 94 105558 * | 5/1994 |
| WO | WO9607907 A1 | 3/1996 |
| WO | WO 97/30344 | 8/1997 |
| WO | WO 98/19159 | 5/1998 |
| WO | WO98/55856 | 12/1998 |

| WO | WO 99/05966 | 2/1999 |
| WO | WO99/13100 | 3/1999 |
| WO | WO 01/23885 A1 | 8/1999 |
| WO | WO01/78992 | 12/2000 |
| WO | WO01/46457 A2 | 6/2001 |
| WO | WO 02/08753 A2 | 1/2002 |
| WO | WO 02/18940 A2 | 3/2002 |
| WO | WO02/057766 A2 | 7/2002 |
| WO | WO03/042691 A1 | 5/2003 |
| WO | WO2004/008130 A1 | 1/2004 |

OTHER PUBLICATIONS

Copending U.S. Appl. No. 10/617,262, filed Jul. 10, 2003, entitled "Enzyme Electrodes And Method of Manufacture" (DUMM:011).

Copending U.S. Appl. No. 10/755,712, filed Jan. 12, 2004, Sensor Dispensing Device (DUMM:013).

Copy of published PCT application WO 01/23855A1 corresponding to copending U.S. Appl. No. 10/089,048, filed Mar. 25, 2002, "Test Device".

Copending U.S. Appl. No. 10/094,501, filed Mar. 8, 2002, "Test Member Orientation".

Copending U.S Appl. No. 10/265,087, filed Oct. 4, 2002, "Test Meter Calibration".

Copending U.S. Appl. No. 10/089,048, filed Mar. 25, 2002, "Test Device".

* cited by examiner

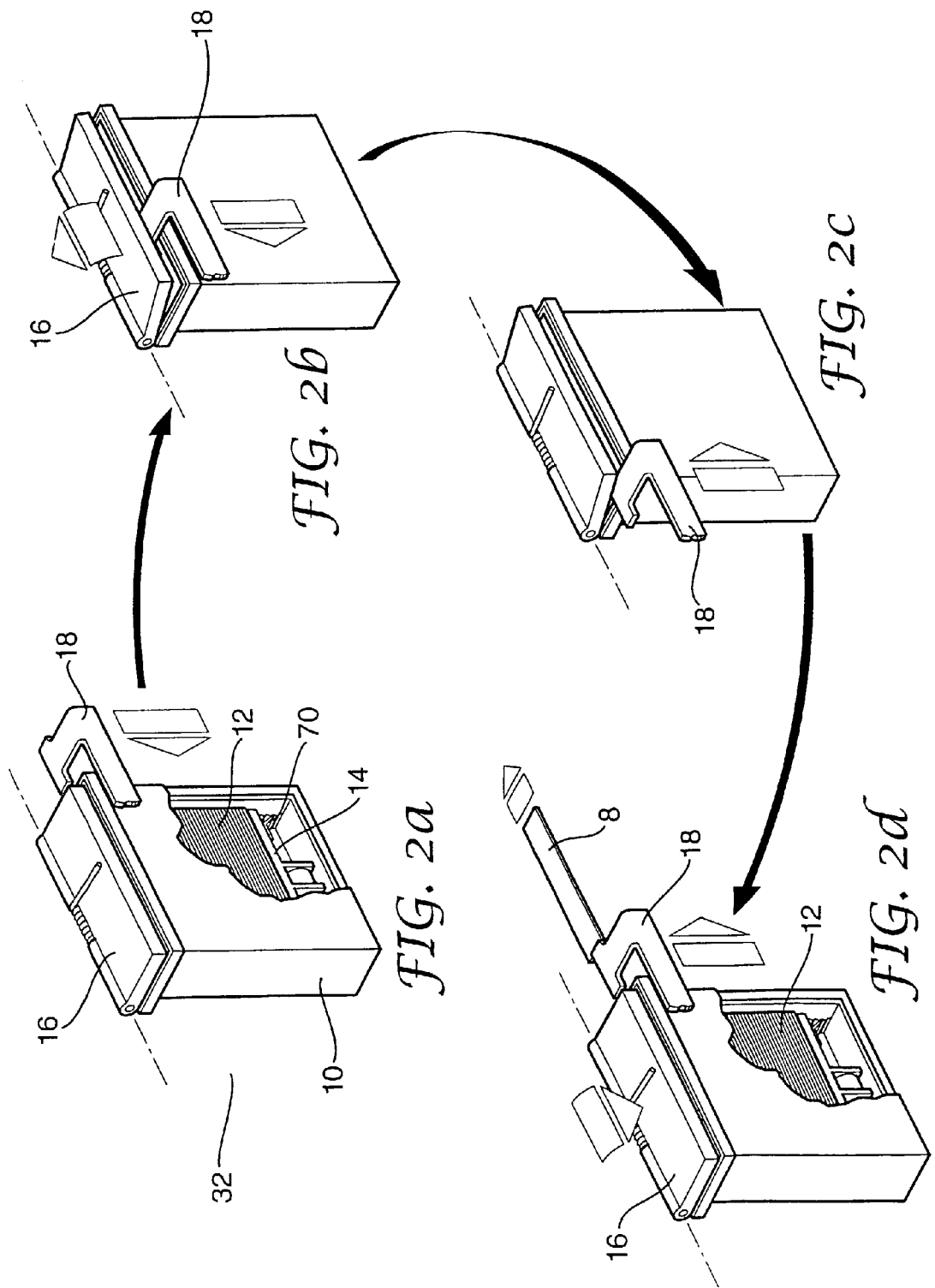

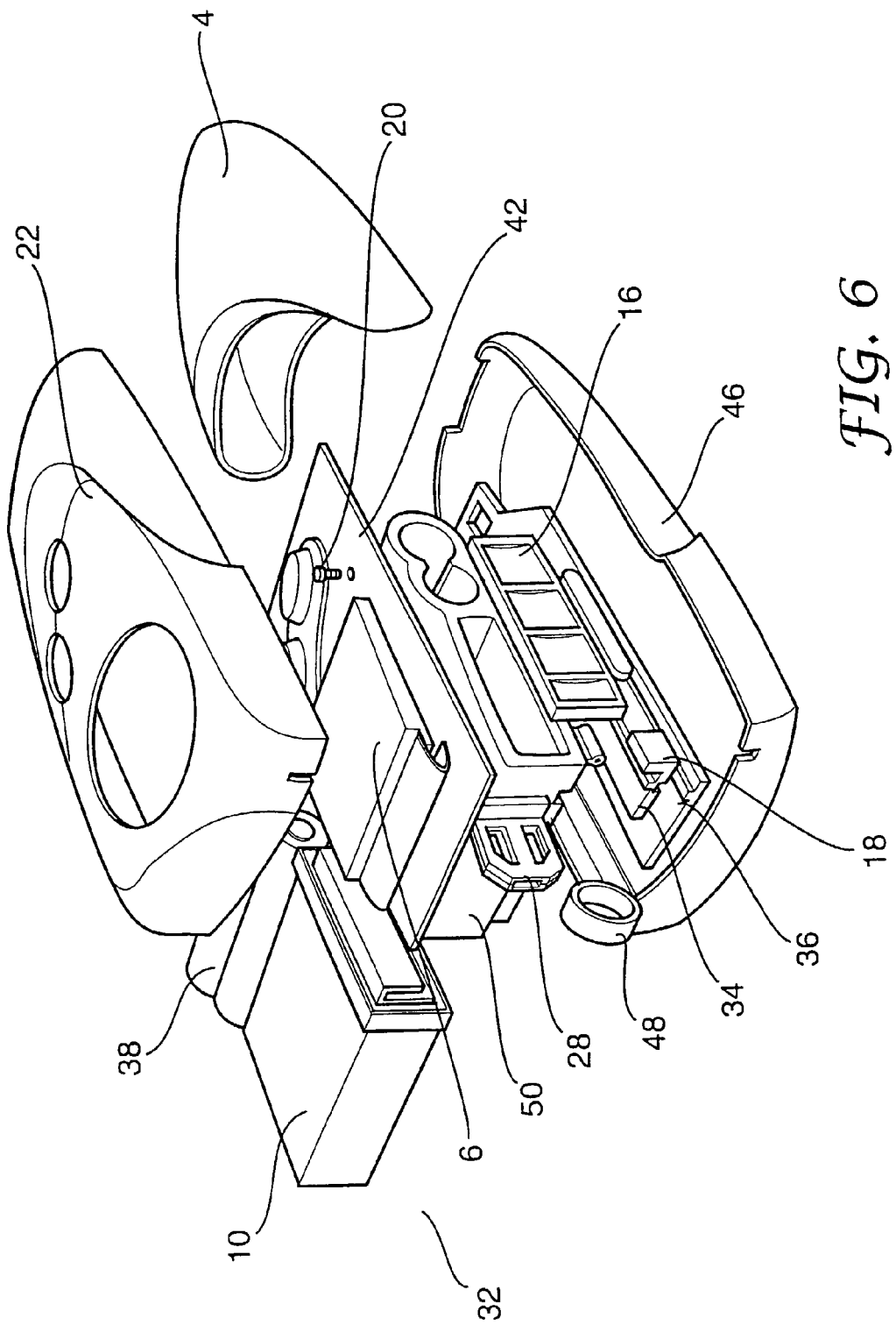

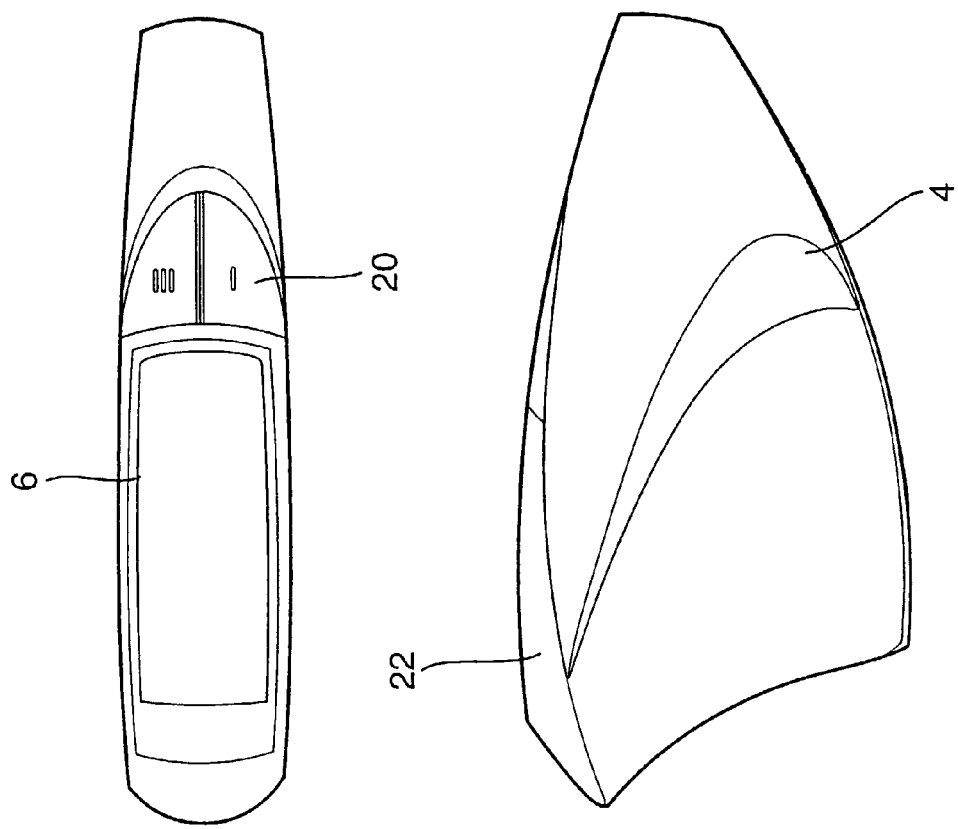
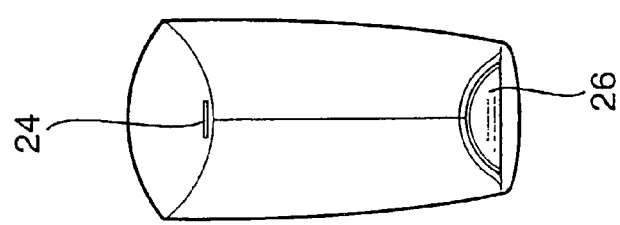
FIG. 7a
FIG. 7b
FIG. 7c

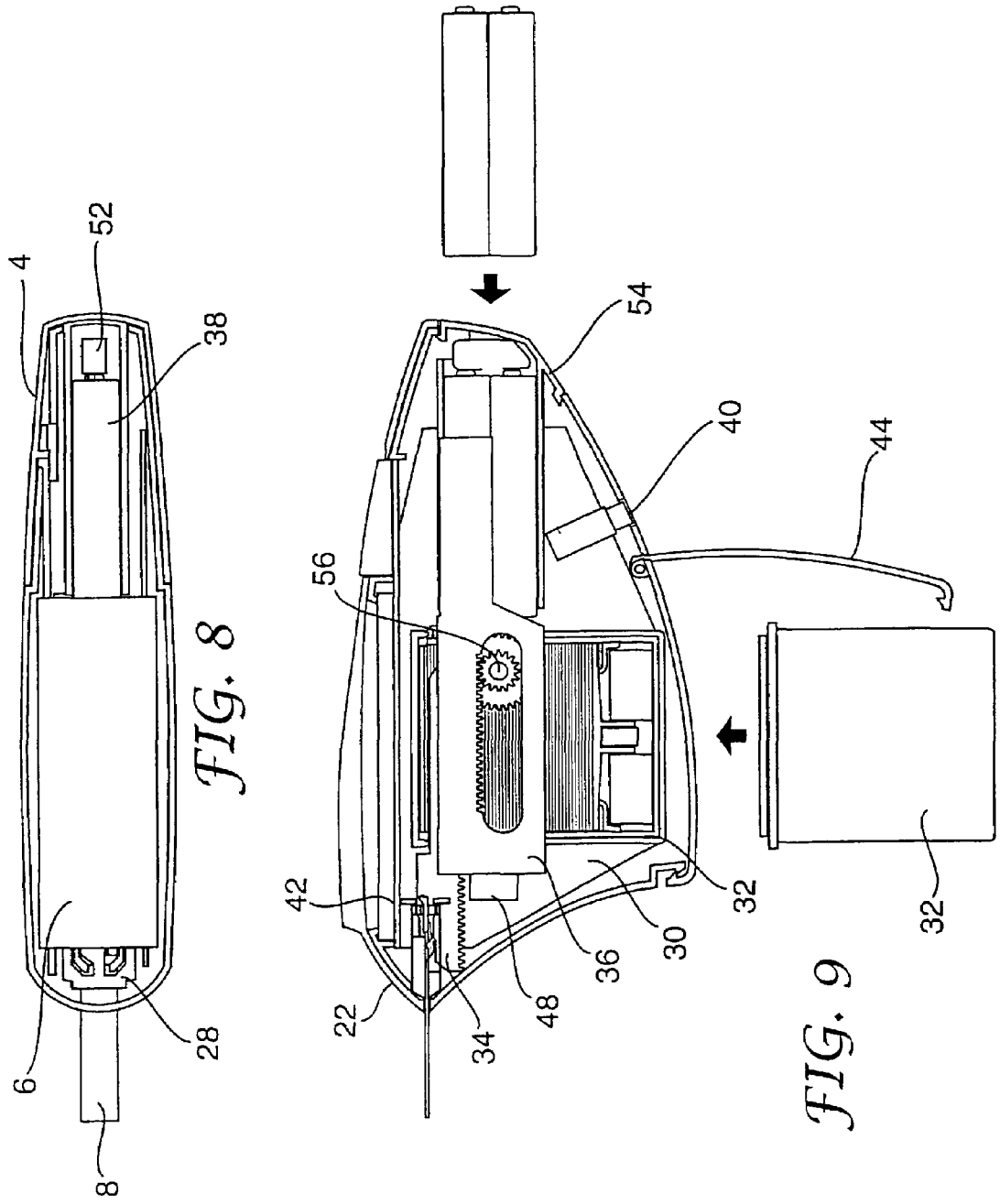

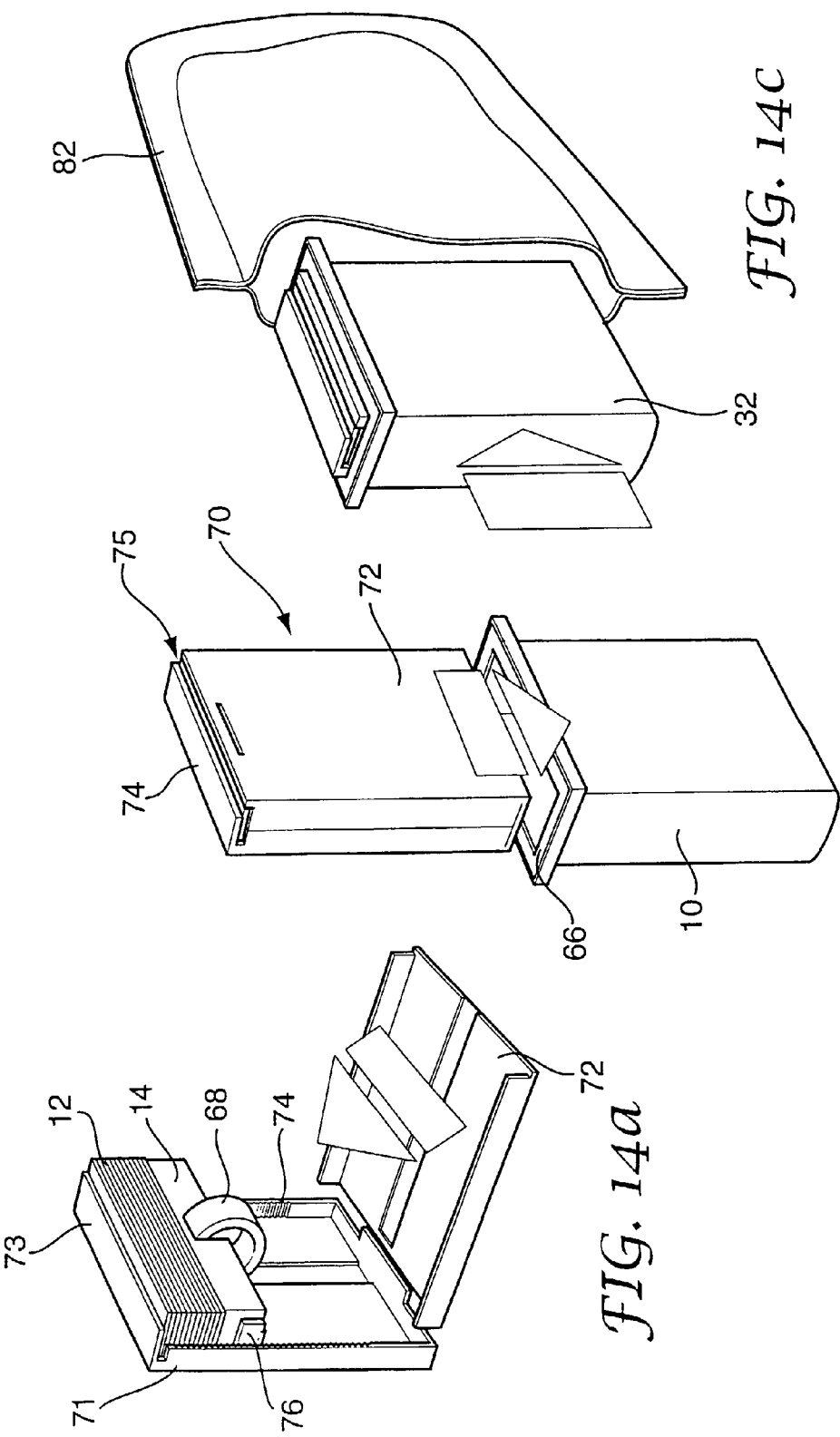

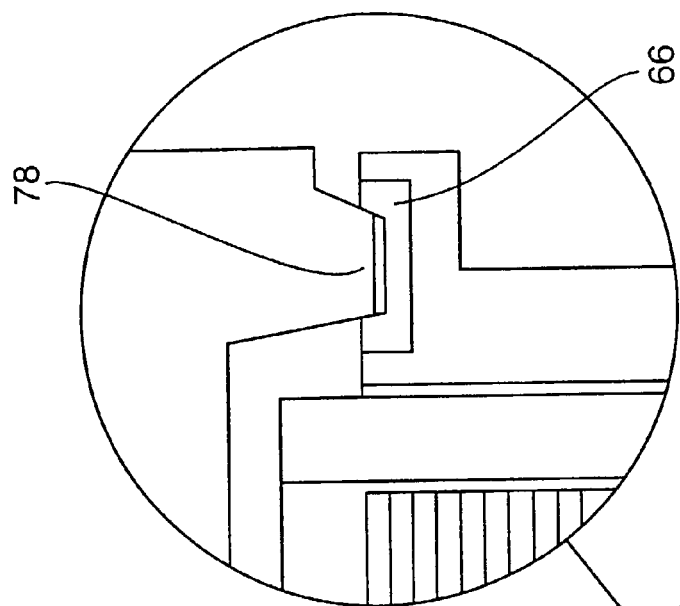
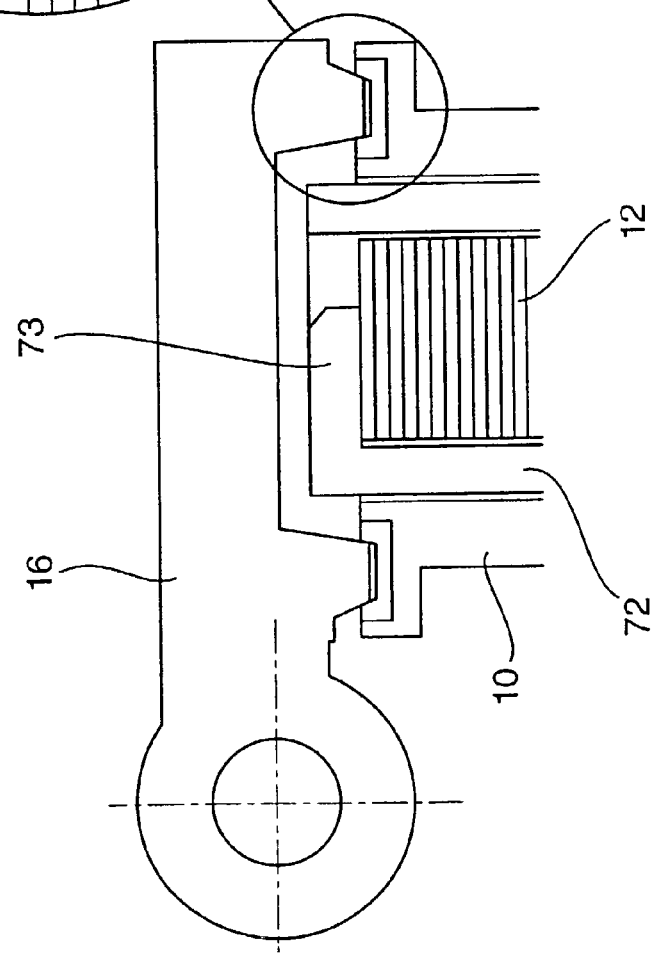

SENSOR DISPENSING DEVICE

This application claims priority to co-pending U.S. provisional application Ser. No. 60/336,921 filed on Dec. 3, 2001 which is entitled "TEST DEVICE," the disclosure of which is incorporated herein by reference. This application also claims priority to British patent application serial number 0127322.6 filed Nov. 14, 2001," the disclosure of which is also incorporated herein by reference.

BACKGROUND OF THE INVENTION

1. Field of the Invention

The present invention relates to a sensor dispensing device for dispensing sensors for measuring the concentration of an analyte in a fluid sample. The invention extends to a cartridge assembly containing sensors for use in the device, and to an inner member for the cartridge assembly.

2. Description of the Prior Art

Diabetics regularly need to test samples of their blood to determine the level of blood glucose. The results of such tests may be used to determine levels of medication needed to treat the diabetes at the time. In one known type of system, disposable sensors are used to test the blood. The sensors typically take the form of test strips which are provided with a reagent material that will react with blood glucose to produce an electrical signal. Conductive tracks on the test strip relay the electrical signal to a meter which displays the result. After a sample of blood has been applied to the test strip and the measurement has been taken, the test strip is disposed of. In order to couple the conductive tracks on a test strip with the meter, the test strip needs to be inserted into a sensor holder prior to the start of testing. The sensor holder has corresponding electrodes which are brought into electrical contact with the conductive tracks of the test strip. Test devices are known in which a plurality of test strip are provided on a cartridge disc. Each strip is housed in its own sensor slot, and means are provided to eject a test strip from its slot when required, and to automatically locate it in a sensor holder. Examples of test devices with test strip dispensers are described in U.S. Pat. No. 5,660,791, and European Patent Application Numbers 0 732 590, 0 738 666, and 0 811 843.

A problem with test strips is that they have only a limited shelf life, and exposure of test strips to the atmosphere further reduces the shelf life.

It has been proposed in WO 94/10558 to provide a stack of disposable sensors in a cylindrical housing, the stack being urged towards a test station to form a liquid-proof seal. In DE 196 39 226 A1 it is proposed to provide a test device with a cartridge that may have a plurality of chambers containing test strips, each of which chambers may be individually sealed to preserve the shelf life of the strips therein. A user removes the seal for each chamber when required, and a timing circuit may be activated either by the user or when the cartridge is pushed into the device. After a set time period has elapsed, an alarm or other indication reminds the user that the time period for using the strips has elapsed.

It is an object of the present invention to provide an improved test device. It is a further object of the invention to provide an improved dispenser for sensors for use in measuring analyte concentration in an applied fluid.

SUMMARY OF THE INVENTION

According to an aspect of the present invention there is provided a sensor dispensing device for dispensing sensors for testing of analyte concentration in a fluid to be applied thereto, the device comprising:

a) a housing having a plurality of sensors arranged in a stack therein, each sensor carrying reagent means for producing a signal in response to the concentration of analyte in an applied fluid;

b) the housing having an opening of sufficient dimensions to permit a sensor to pass through the opening;

c) a stop member located beyond the opening which limits outward travel of sensors from the stack;

d) a spring means which urges the sensors towards the stop member;

e) a fixed gap between the stop member and the said opening of suitable dimensions to permit a sensor to be pushed through the said gap;

f) a sealing member for forming a moisture-tight seal with at least one sealing surface on or around the housing so as to protect sensors in the housing from atmospheric moisture, the relative positions of the sealing member and the sealing surface being adjustable by externally-actuable means to make or break the said seal; and g) an externally-actuable pushing member for pushing a sensor from the said stack through the said gap to a dispensed position.

The sensor in the dispensed position may be taken by the user and used in a conventional test meter. In a preferred embodiment, however, the device further comprises signal-reading means for determining the concentration of an analyte in an applied sample according to a signal generated by the sensor in the dispensed position. The signal-reading means may comprise electronic circuitry for measuring an electric signal generated by the sensor in response to analyte concentration in an applied sample. With the sensor in the dispensed position its electrodes engage with contacts connected to the circuitry, in known manner. Alternatively, the signal-reading means may measure an optical change in the sensor, for example a colour change. Many suitable signal-reading means are known to those skilled in the art.

By providing the stop member on the housing or on a support around the housing the sensors may be provided in a pre-assembled cartridge which can be inserted into the dispenser or into a test device and be ready for use without further user actions.

The stop member may be a wall of the housing so that the housing comprises a box which is closed save for a fixed gap on one wall through which the sensors are pushed, and a gap through which the pushing member is disposed when pushing a sensor. Alternatively the stop member could extend across only a part of the opening, sufficient to prevent sensors from being urged out of the housing by the spring means. In this case, there may be a single gap which extends along one wall of the housing.

The gap could be dimensioned to permit a plurality of sensors to be pushed simultaneously from the housing; however it is preferred that the gap is set such that only one sensor can pass through at a time, to prevent accidental dispensing of more than one sensor. In a preferred embodiment, the sensor adjacent to the stop member is dispensed through the gap.

The sealing member may comprise a cap, the cap and housing being movable relative to each other between an open position wherein a sensor can pass between the cap and the housing and a closed position in which the cap is urged against the sealing surface, at least one of the cap and the sealing surface being provided with sealing means for making a moisture-tight seal therebetween when the cap is in the closed position. The sealing means may be formed from any suitable material well known to persons skilled in the art, for example natural or synthetic rubbers, including foam rubbers. Preferred materials are thermoplastic elastomers, for example Santoprene™, a nitrile rubber mixed with polypropylene, or thermoplastic polyurethane elastomers, for example Pellethane™. Santoprene™ elastomer is particularly preferred because it can be processed by injection moulding.

In a preferred embodiment, the cap makes a seal with a peripheral sealing surface around the housing. However, it would also be possible for the cap to act as a plug and make a seal by fitting inside the housing.

The invention provides a sensor dispensing device which can keep sensors sealed from moisture when the device is not in use and quickly dispense a single test strip for use when required.

The externally actuable means are preferably actuated mechanically by a user moving an external actuator, for example a movable sleeve or handle on the dispenser or test device. Additionally, or alternatively, actuation may involve one or more electric or other motorised means; for example a user may press a button which operates a motor.

The movement of the pushing member may be in the same direction as that of the external sleeve or handle, or it may be at an angle, notably perpendicular to the direction of movement of the external actuator, by means of a series of linkages which convert translational motion to rotational motion and vice versa.

In a preferred embodiment, adjustment of the cap to the open position and movement of the pushing member are actuated by adjustment of a single external actuator. It is particularly preferred that the pushing member itself acts to adjust the cap to the open position. The pushing member may be a slider which from an initial rest position slides so as to insert itself between the cap and the housing, thereby adjusting the cap to the open position, and which subsequently pushes a sensor from the stack to the engagement location. Preferably the arrangement is such that the pushing member undergoes reciprocal movement.

The invention will be described with reference to the testing of glucose concentrations in blood, but it will be understood that the invention is not limited to this embodiment and is of general applicability for testing analytes in bodily and other fluids.

The sensors will typically comprise test strips of a type known per se, and the invention will be described herein with reference to the use of such test strips. However it will be understood that the invention is not limited to the use of conventional test strips and that other alternative sensors may be used.

The cartridge assembly is preferably removable, and may be sold as a separate item for refilling the test device. Accordingly, another aspect of the invention provides a cartridge assembly comprising:
a) a housing having a plurality of sensors arranged in a stack therein, each sensor carrying reagent means for producing a signal in response to the concentration of analyte in an applied fluid;
b) the housing having an opening of sufficient dimensions to permit a sensor to pass through the opening;
c) a stop member located beyond the opening which limits outward travel of sensors from the stack;
d) a spring means which urges the sensors towards and into contact with the stop member;
e) a fixed gap between the stop member and the said opening of suitable dimensions to permit a sensor to be pushed through the said gap; and
f) at least one sealing surface on or around the housing for making a moisture-tight seal with a suitable sealing member so as to protect sensors in the housing from atmospheric moisture.

In a preferred embodiment the sealing surface is provided by a support member in which the housing is received. In this embodiment, the housing comprises a cartridge inner member and the support member comprises a cartridge outer member.

The cartridge inner member may be sold and dealt in separately, so that the cartridge outer is retained and only the inner member replaced when necessary. Accordingly, a further aspect of the invention provides a cartridge inner member comprising:
a) a housing having a plurality of sensors arranged in a stack therein, each sensor carrying reagent means for producing a signal in response to the concentration of analyte in an applied fluid;
b) the housing having an opening of sufficient dimensions to permit a sensor to pass through the opening;
c) a stop member located beyond the opening which limits outward travel of sensors from the stack;
d) a spring means which urges the sensors towards and into contact with the stop member;
e) a fixed gap between the stop member and the said opening of suitable dimensions to permit a sensor to be pushed through the said gap;

wherein the opening of the housing has two opposed long edges and two opposed short edges, the stop member being attached to or integrally formed with one of the said long edges, and the said gap being laterally accessible through a channel disposed substantially parallel to and extending along the entire length of the other of the said long edges.

The housing may contain a desiccant to absorb moisture. In a preferred embodiment, the housing or a component thereof, for example a sprung follower, may be formed from a desiccant plastics material. Suitable desiccant plastics materials are known in the art and may be obtained from CSP Technologies, Bourne End, Bucks, UK.

Any suitable spring means may be used and are well known to those skilled in the art. Examples are coil or compression springs, elastic members, or pneumatic or motorised pushing members. It is preferred that the spring means are constant tension springs to provide controlled movement of the stack within the housing.

The cartridge may be removable so that the dispenser or test device may be re-used with a new cartridge. In another embodiment, the cartridge is loaded in the test device during manufacture and is not removable. The device is disposed of once the sensors have all been used or when their useful life has been exceeded. With this arrangement a single general-purpose meter can be manufactured, the function of which depends on which type of sensors are in the cartridge which is loaded.

Other aspects and benefits of the invention will appear in the following specification, drawings and claims.

BRIEF DESCRIPTION OF THE DRAWINGS

The invention will now be further described, by way of example, with reference to the following drawings in which:

FIG. 2 illustrates a mechanical sequence for dispensing a sensor from a stack of sensors in a device in accordance with embodiments of the present invention;

FIG. 6 is an exploded drawing of the device of FIG. 3;

FIG. 7 shows external views of a third embodiment of a sensor dispensing device in accordance with the present invention;

FIGS. 8 and 9 show part-sectional views of the device of FIG. 7;

FIG. 14 shows steps in the manufacture of an alternative embodiment of a replacement cartridge assembly for use in a sensor dispensing device according to the invention;

FIGS. 15 and 16 show details of the sealing arrangement of an embodiment of a sensor dispensing device in accordance with the invention;

DETAILED DESCRIPTION

Figure 1B:
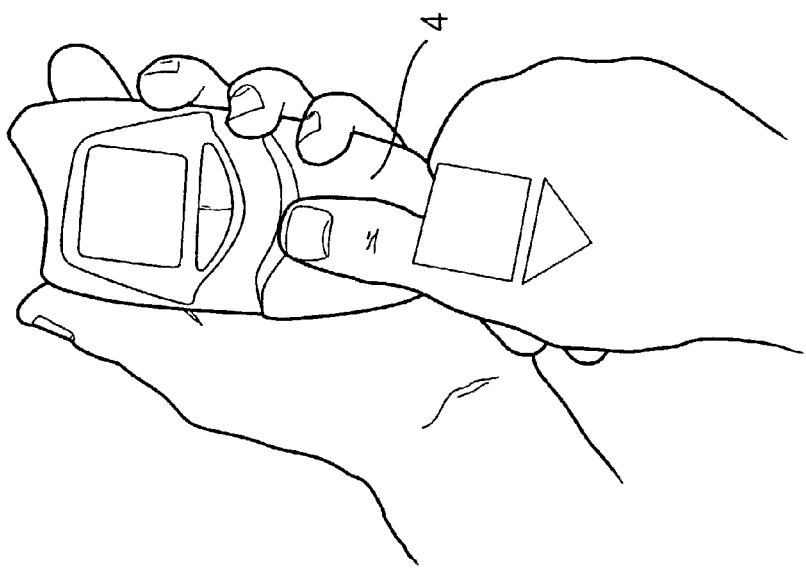
FIG. 1 shows user actions for taking a blood glucose reading using a first embodiment of a sensor dispensing device in accordance with the present invention.
Figure 1A:
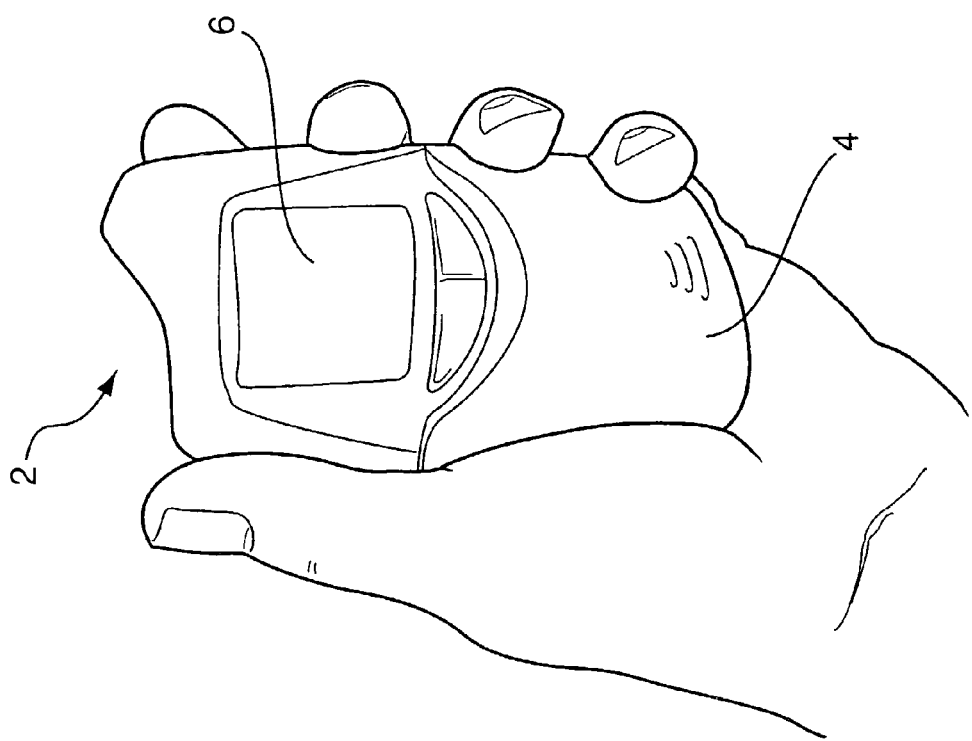
Figure 1D:
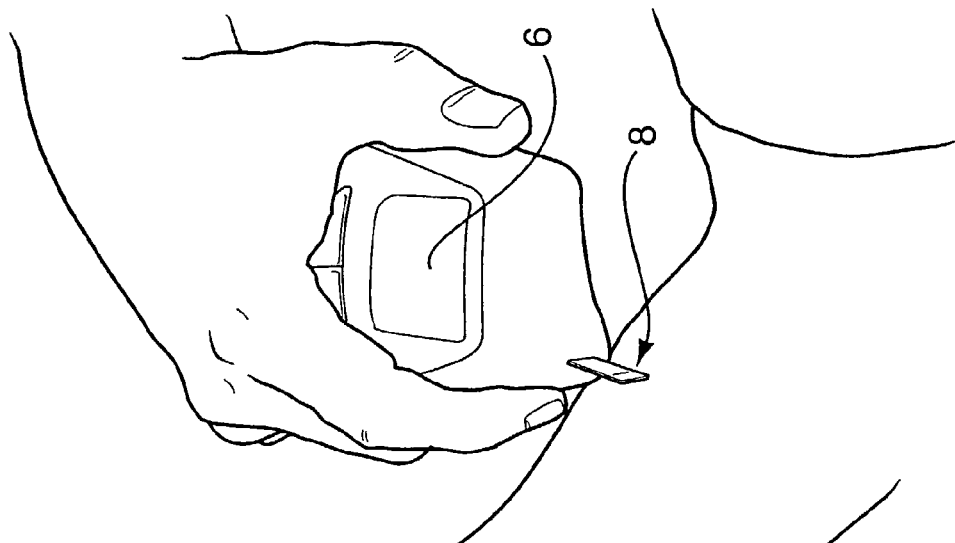
Figure 1C:
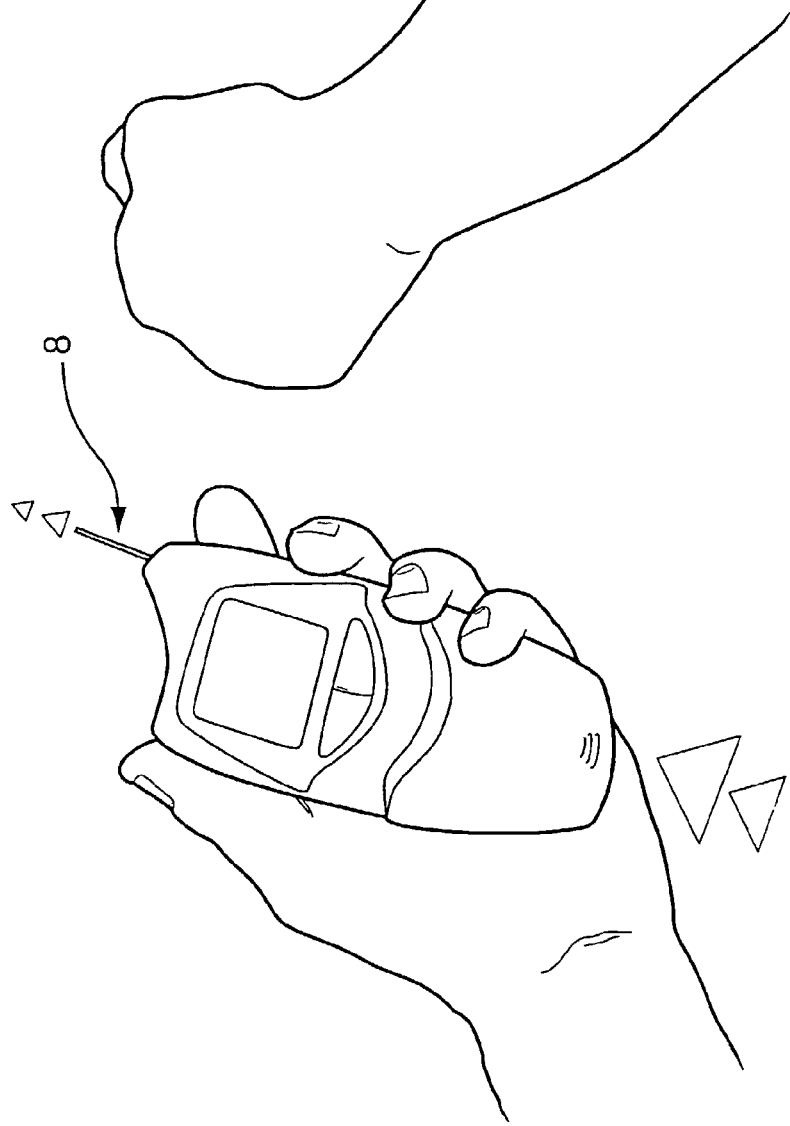
Figure 3C:
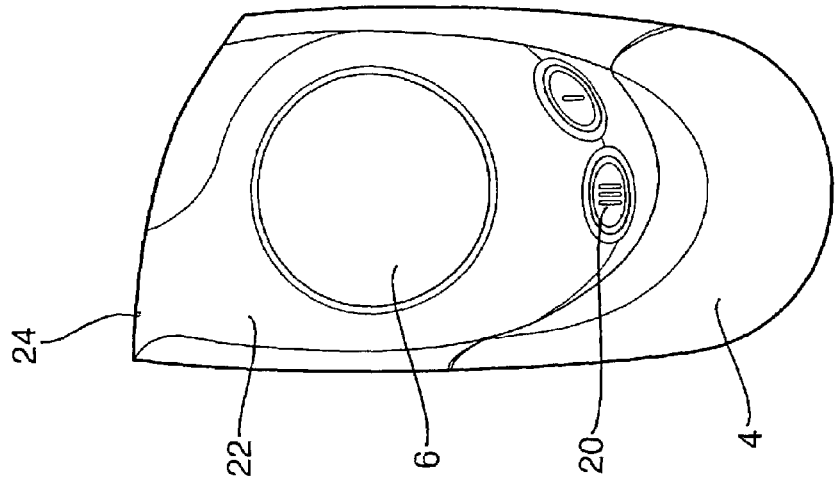
FIG. 3 shows external views of a second embodiment of a sensor dispensing device in accordance with the present invention.
Figure 3B:
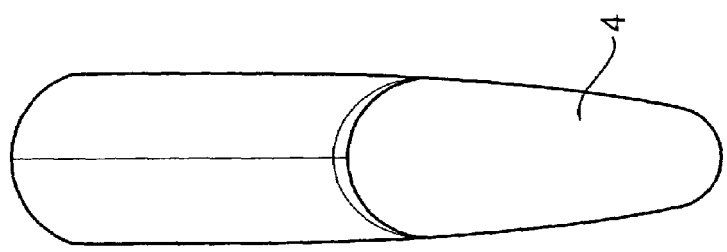
Figure 3A:
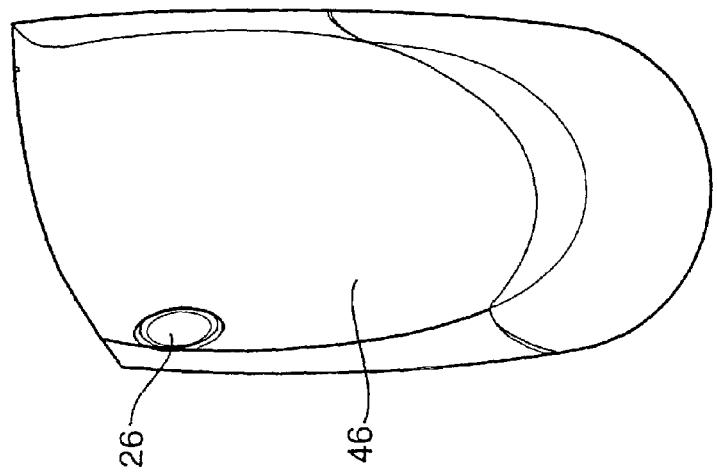
Figure 5:
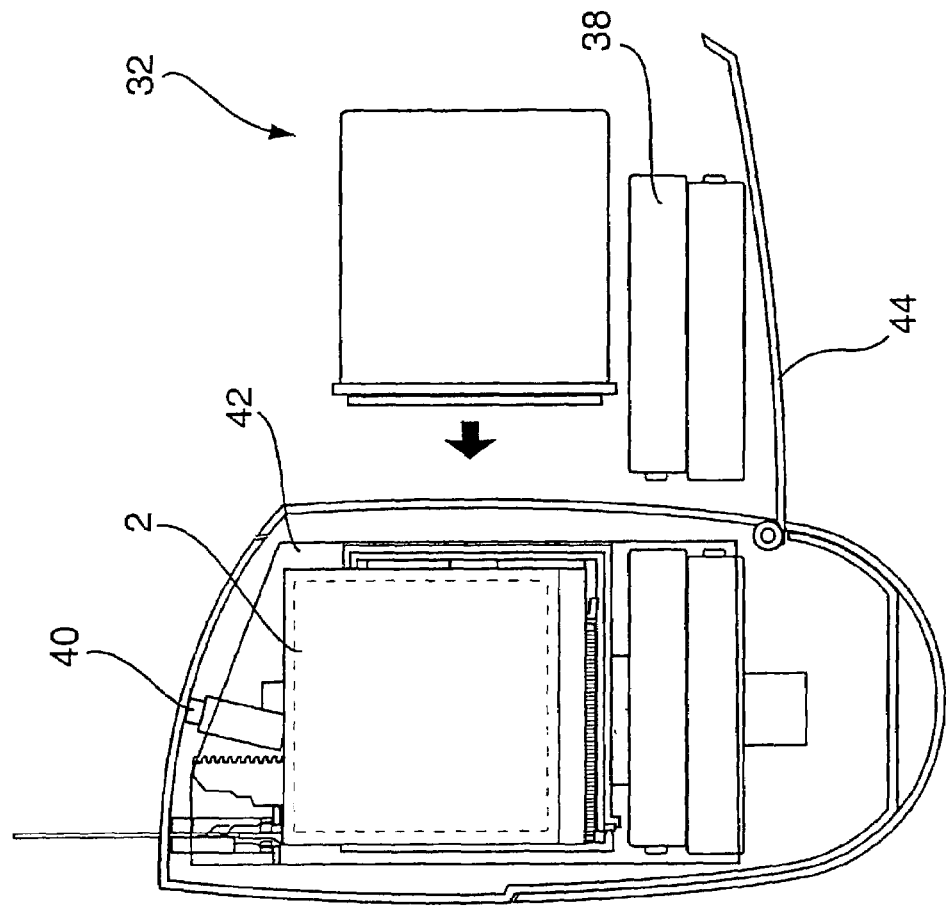
FIGS. 4 and 5 show part-sectional views of the device of FIG. 3.
Figure 4:
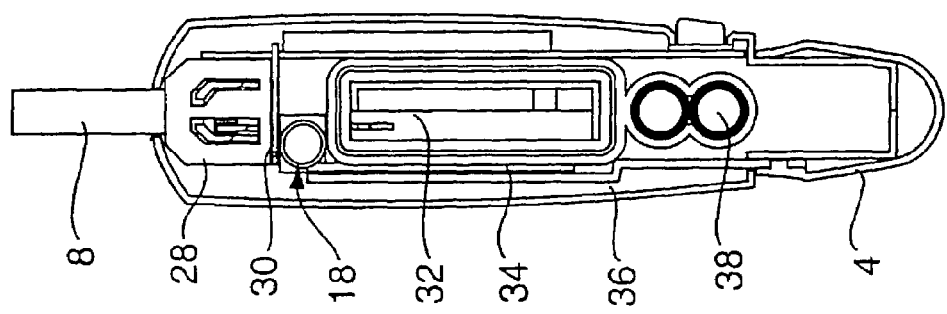
Figure 10:
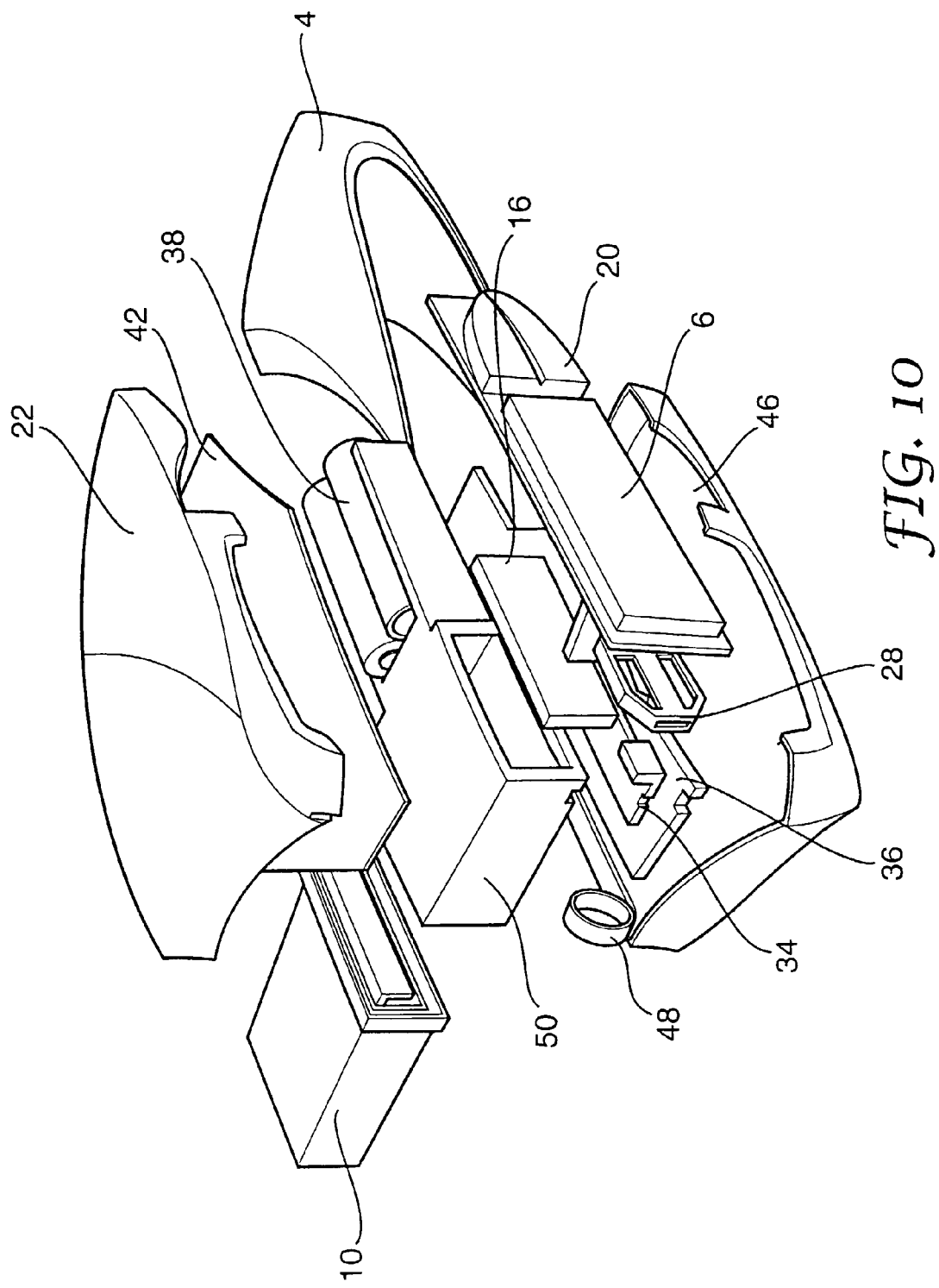
FIG. 10 is an exploded drawing of the device of FIG. 3.

In the following description the same numbers will be used to refer to equivalent parts of the various embodiments.

Referring to FIG. 1, the sensor dispensing device 2 can be held in a user's hand. The device 2 has an external slidable sleeve 4 and a display 6, in this example an LCD. From the rest position of FIG. 1a, the user pulls back the actuating sleeve 4 (FIG. 1b) against a spring force. As will be explained later, this action opens the cap on a stack of sensors in a housing. The user releases the sleeve 4 (FIG. 1c) and the spring force returns the sleeve 4 to the rest position, in the process of which the device is activated to take a reading, a sensor 8, in this example a test strip, is presented to receive a drop of blood, and the cap returns to make a seal with the housing. The user applies a sample of blood to the sensor 8 (FIG. 1d) and the glucose value is shown on the LCD 6. The used sensor 8 is then discarded.

FIG. 2 illustrates schematically the mechanical sequence of events occurring inside the device 2. A cartridge assembly 32 comprises a cartridge outer 10 which encloses a cartridge inner 70. The cartridge inner 70 is a housing which has a single opening covered by a spring-biased cap 16. In the rest position shown in FIG. 2a, the cap 16 is pressed against the cartridge outer 10 to make a moisture-tight seal. In the housing 70 is a stack 12 of test strips 8, urged towards the cap 16 by a sprung follower 14. A stop member (best illustrated in FIGS. 13 and 14) limits outward travel of the test strips 8 towards the cap 16, and the stack 12 bears against the stop member. A slider 18 outside the cartridge assembly 32 is operatively connected to the sleeve 4. As the user pulls the sleeve 4 back, the slider 18 is pulled backwards. As the slider 18 moves backwards (FIG. 2b) a leading edge of the slider 18 is inserted between the cartridge outer 10 and the cap 16, initially forcing the cap 16 upwards and then forcing the stack 12 down slightly against the spring force. When the slider 18 has passed fully over the stack 12 (FIG. 2c), the sprung follower 14 urges the top test strip 8 up into the return path of the slider 18. As the slider 18 is returned back to the rest position it moves the top test strip 8 to an engagement location at which its electrodes engage with contacts of the test device. At this point (FIG. 2d) the slider 18 has removed itself from between the cartridge outer 10 and the cap 16 so that the cap 16 once again seals against the cartridge outer 10. The test strip 8 is ready for use.

Figure 17:
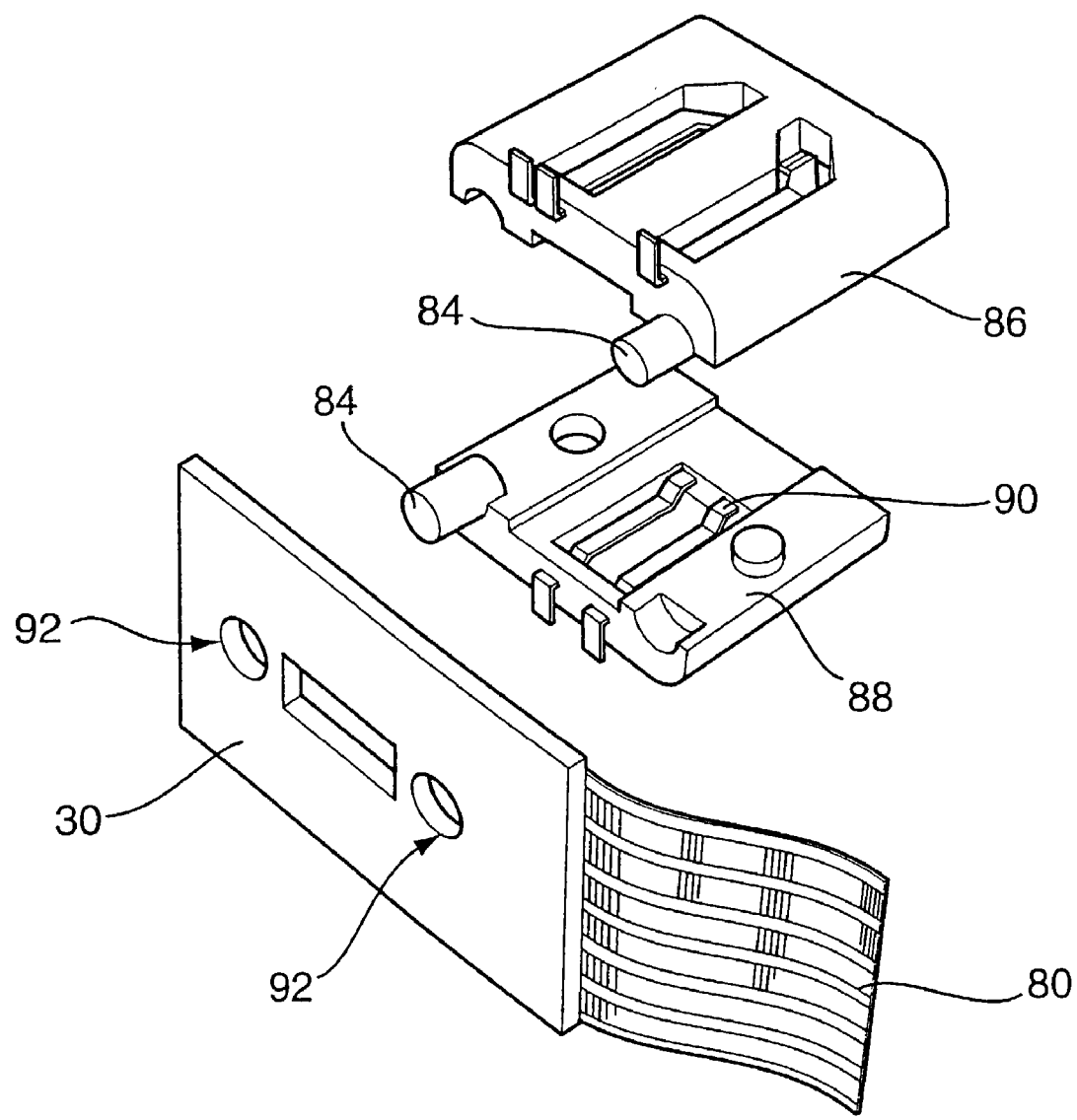
FIG. 17 is an exploded view of a preferred contact assembly for a sensor dispensing device in accordance with the invention.

Referring now to FIGS. 3 to 6, a second embodiment of the invention is described. The actuating sleeve 4 is mounted either side of the upper 22 and lower 46 meter casings. The sleeve 4 accommodates left and right handed users and allows various gripping strategies. The meter casing 22, in this example formed from an acrylic material, is provided with a front-mounted LCD 6, key-pad function buttons 20, and strip ejection slot 24. The LCD key-pad, and other meter electronics components are mounted on a main PCB 42 which is in turn connected to a second PCB 30. The second PCB 30 is electrically connected to a contact block 28, with which the electrodes of the test strip 8 engage when the strip is in the engagement location, as best shown in FIG. 17.

Cartridge access from the side of the device is provided by a cartridge cover 44 which is opened by operation of a release button 26. In this example the cartridge cover 44 provides access to batteries 38 in addition to the cartridge assembly 32. The batteries 38 and cartridge assembly 32 are received in a single moulded chassis 50. A download socket 40 is provided for downloading external data such as calibration values for the test strips. The sleeve 4 is connected to an actuator rack 36 which is connected to a strip-pusher rack 34 via a pinion gear arrangement (not shown in FIGS. 3–6—illustrated in FIG. 9). When the user pulls back the sleeve 4, the actuator rack 36 causes the strip-pusher rack 34 to move a greater distance because of the pinion gear-ratio. The strip-pusher rack 34 is connected to the slider 18 which operates as described with reference to FIG. 2 above. A return spring 48 acts to return the sleeve 4 to the rest position after it has been pulled back and released.

A third embodiment of the invention is illustrated with reference to FIGS. 7 to 10. In this embodiment the LCD 6 is side-mounted to maximise the gripping area without obscuring the screen. This arrangement facilitates holding the device with a precision pen-style grip as well as in a fist. The strip ejection point 24 is situated at an edge projection, which helps to indicate to the user where the strip will emerge from. A separate battery cover 54 is provided, which has a battery contact member 52 provided on its inner surface. As illustrated in FIG. 9, the actuator rack 36 engages with the smaller wheel of a pinion gear 56, while the strip-pusher rack 34 is driven by the larger wheel of the pinion gear.

Figure 12:
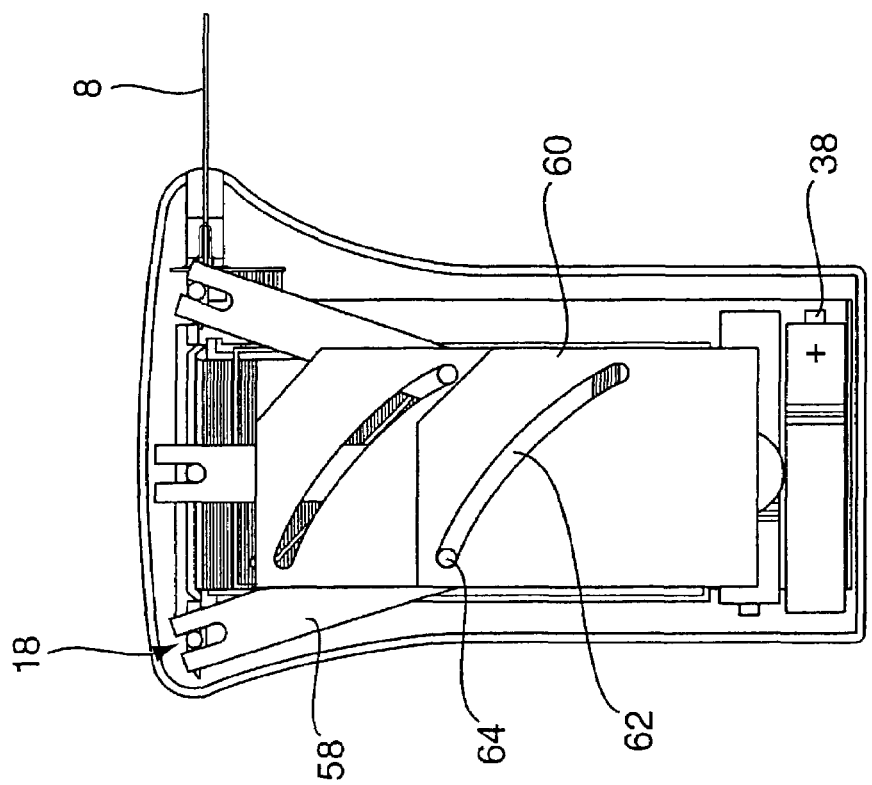
FIGS. 11 and 12 are part-sectional views of a fourth embodiment of a sensor dispensing device in accordance with the present invention.
Figure 11:
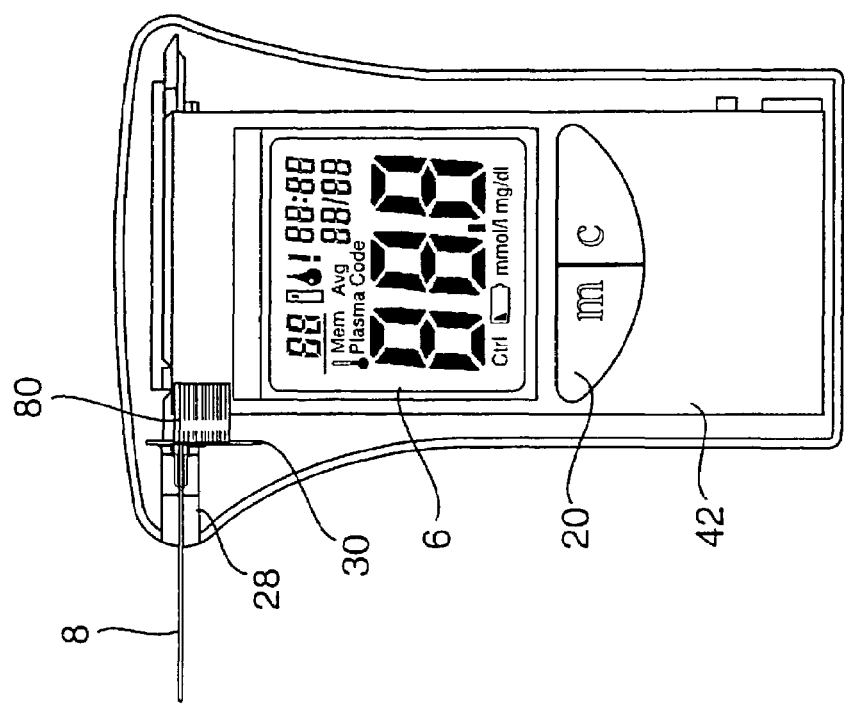

A fourth embodiment of the device is shown in FIGS. 11 and 12, which employs an alternative mechanism for driving the slider 18. Here, the sleeve (not shown) is directly connected to an actuating plate 60 which has an arcuate slot 62 therein. The slider 18 is provided with a projection that sits in a slot at one end of a pivot arm 58. The arrangement is such that turning of the pivot arm 58 produces linear translation of the slider 58 by virtue of lost motion in the slot. The pivot arm 58 is provided with a projection or pin 64 which is disposed in the arcuate slot 62 so that sliding of the actuating plate 60 causes pivoting of the pivot arm 58 and hence sliding of the slider 18. Referring to FIG. 12, it will be seen that sliding the actuating plate 60 from the upper position (shown in white) to the lower position (shaded)

causes the slider 18 to move from the rest position shown on the extreme right, to the position shown on the extreme left. Reversal of this movement, for example by means of a spring, dispenses the test strip 8 as previously described.

Figure 13:
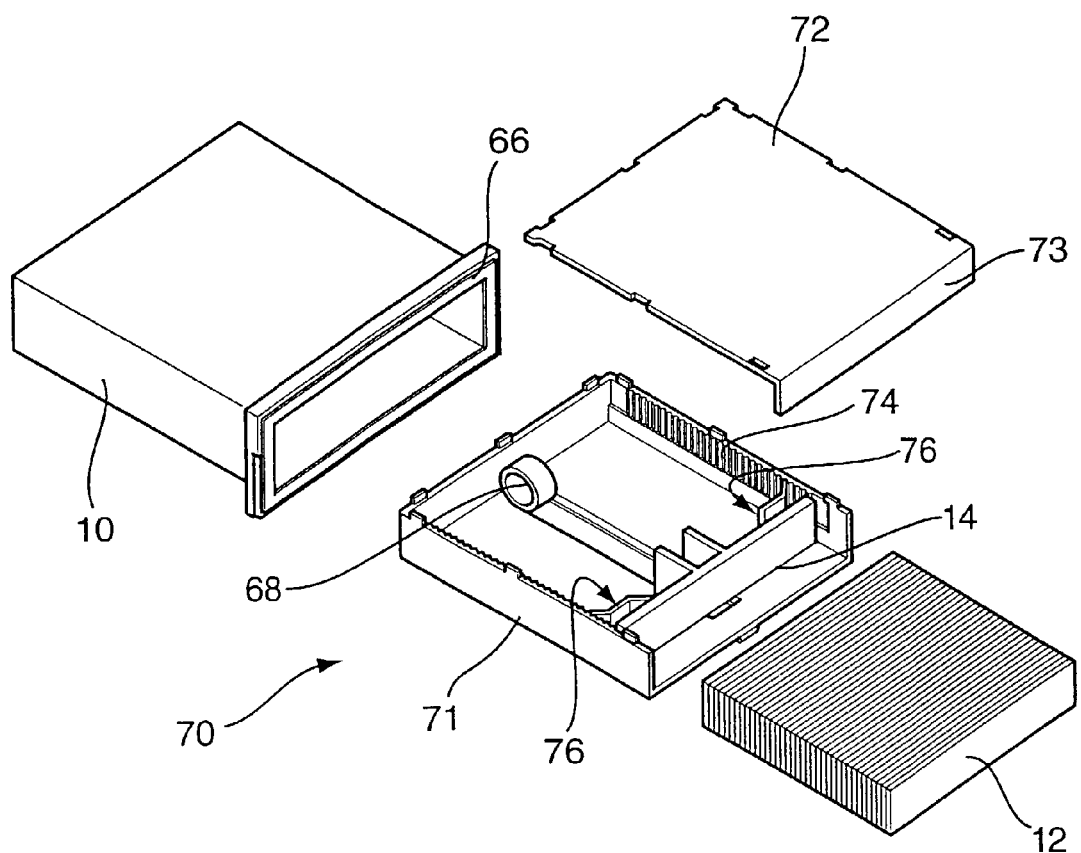
FIG. 13 is an exploded view of a cartridge assembly for use in a sensor dispensing device according to the invention.

One way of manufacturing the cartridge assembly 32 is illustrated in the exploded diagram shown in FIG. 13. The assembly comprises a cartridge outer 10 which has a single opening. A resilient seal 66, for example of a thermoplastic elastomer, is provided around the opening. Within the cartridge outer 10 is a cartridge inner 70 which houses a constant tension spring 68 operatively connected to a follower 14. The cartridge inner 70 is formed from a base member 71 and a closure member 72. Two opposed upstanding walls of the base member 71 are provided with a series of ridges 74 in which fit arms 76 of the follower 14. The ridges 74 and arms 76 are profiled to permit movement of the follower 14 in one direction only, towards the stack 12 of test strips. During assembly, the follower 14 is located near to the spring 68 to permit the stack 12 to fit in the cartridge inner 70. The closure member 72 is snap-fitted on the base member 71 to form the cartridge inner 70 which is located in the cartridge outer 10. A lip 73 on the closure member 72 provides a stop member which limits outward travel of the stack 12. There is a sufficient gap between the lip 73 and the adjacent walls of the base member 71 (which define an opening of the housing) to permit a single strip 8 to slide out axially, as illustrated with reference to FIG. 2.

An alternative cartridge assembly design, for a replacement cartridge assembly 32, is shown in FIG. 14. Here the stop member 73 is provided on the base member 71. After closing the closure member 72 (FIG. 14a) the cartridge inner 70 is put in the cartridge outer 10 (FIG. 14b) to form the cartridge assembly 32. An elongate channel 75 is disposed parallel to the top edge of the closure member 72, allowing access of a pushing member, from the side or the top as viewed, to push out the test strip adjacent to the stop member 73. Finally the cartridge assembly 32 is put in a foil bag 82 (FIG. 14c) and sealed. The bag may be provided with a desiccant to keep the cartridge assembly 32 in a low moisture environment.

It is preferred that the cartridge assembly 32 comprise both the cartridge inner 70 and the cartridge outer 10, so that both these elements are replaced together. This arrangement ensures that the resilient seal 66 is periodically replaced. However, it will be appreciated that the cartridge inner 70 could be separately replaced and the cartridge outer 10 could be re-used.

Referring now to FIGS. 15 and 16, these illustrate a preferred embodiment in which the cap 16 is provided with a profiled wall 78 that fits into and engages with the resilient seal 66 to form a moisture-tight seal when the cap is in the closed position.

Figure 18:
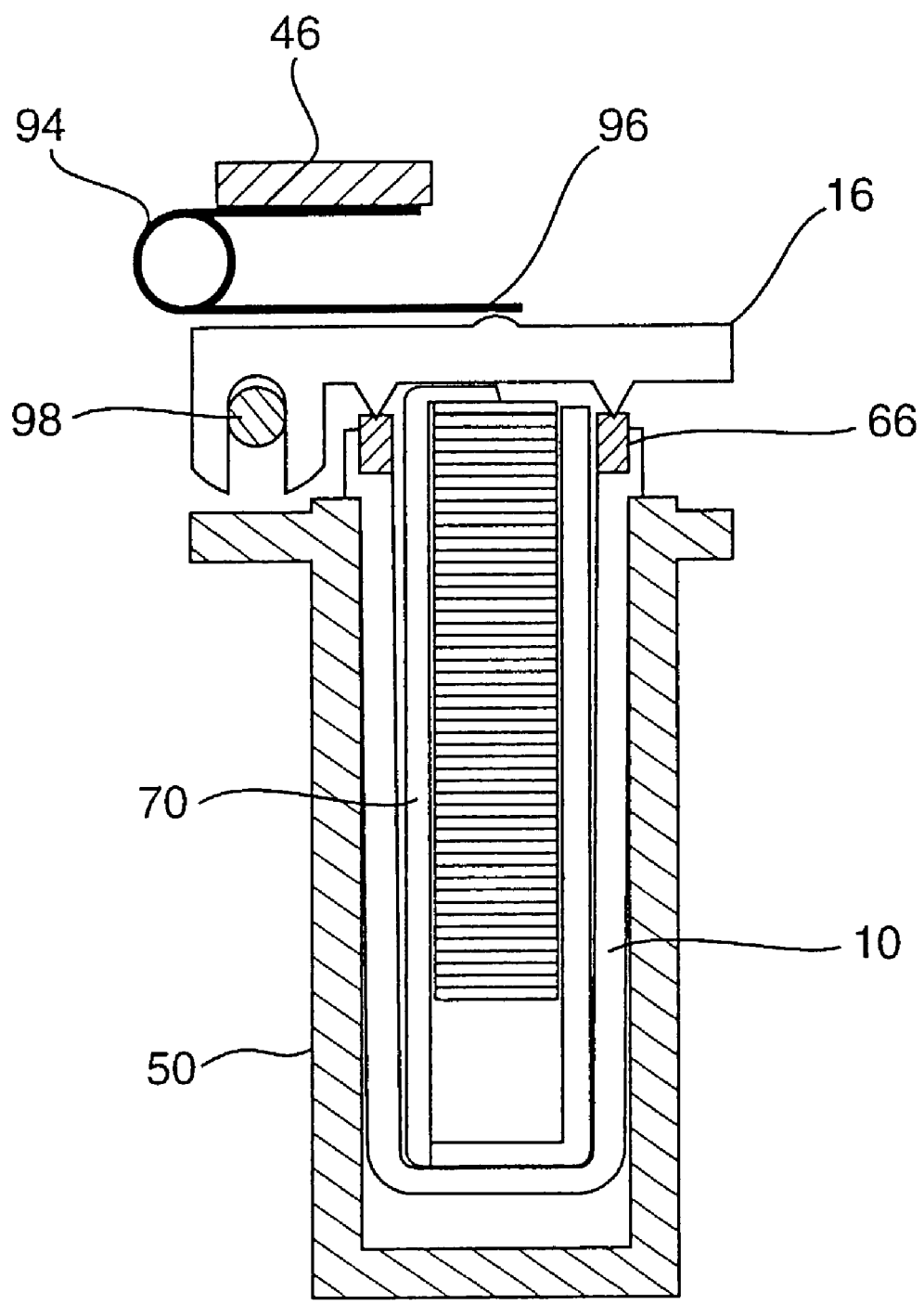
FIG. 18 is a sectional view of a preferred sealing arrangement of a device in accordance with the invention.

In the sealing arrangement shown in FIG. 18, the cap 16 is pivotally mounted on a fixed pivot 98 and urged into sealing engagement with the resilient seal 66 by a spring 94. The arrangement is such that the spring force is exerted at a central point 96 on the cap 16, thereby helping to spread the spring force evenly around the entire periphery of the seal 66 to facilitate complete closure of the cap 16 and sealing of the cartridge inner 70 from atmospheric moisture.

In a preferred embodiment, the sensor dispensing device has an insert moulded contact block 28 to reduce tolerance issues and assembly costs. A preferred construction of the contact block 28 is illustrated in FIG. 17. The contact block 28 is formed from a first 86 and a second 88 moulded member which fit together. Each moulded member is provided with a location pin 84 to engage in recesses in the chassis through holes 92 in the PCB 30. Contacts 90 in the second moulded member engage with electrodes on the test strip 8 and are electrically connected with the main PCB 42 via a flexible connector 80.

Although the invention has been described with reference to a sensor dispensing device or test device for measuring blood glucose concentration, it is to be understood that the invention is not limited to this application. The invention may be used in the determination of any analyte in a fluid, biological or otherwise, by the use of suitable reagents in the test strip. Such reagents are well known to those skilled in the art.

It is appreciated that certain features of the invention, which are for clarity described in the context of separate embodiments, may also be provided in combination in a single embodiment. Conversely, various features of the invention which are, for the sake of brevity, described in the context of a single embodiment, may also be provided separately or in any suitable subcombination.

While the present invention has been described with reference to specific embodiments, it should be understood that modifications and variations of the invention may be constructed without departing from the spirit and scope of the invention set forth in the following claims.

What is claimed is:

1. A cartridge assembly for use in a test device for testing of analyte concentration in a fluid to be applied thereto, the cartridge assembly comprising:
   a) a housing having a plurality of sensors arranged in a stack therein, each sensor carrying reagent means for producing a signal in response to the concentration of analyte in an applied fluid;
   b) the housing having an opening of sufficient dimensions to permit a sensor to pass through the opening;
   c) a stop member located beyond the opening which limits outward travel of sensors from the stack;
   d) a spring means which urges the sensors towards and into contact with the stop member;
   e) a fixed gap between the stop member and the said opening of suitable dimensions to permit a sensor to be pushed through the said gap; and
   f) at least one sealing surface on or around the housing for making a moisture-tight seal with a suitable sealing member so as to protect sensors in the housing from atmospheric moisture;
   g) wherein the housing comprises a cartridge inner member; and
   h) wherein the cartridge assembly further comprises a cartridge outer member in which the cartridge inner member is located, the sealing surface being provided around the periphery of the cartridge outer member.

2. A cartridge assembly as claimed in claim 1, wherein the said sealing surface is provided on a flange around the cartridge outer member.

3. A cartridge assembly as claimed in claim 1, wherein the opening of the housing has two opposed edges, the stop member being attached to or integrally formed with one of the said opposed edges and spaced apart from at least a portion of the other opposed edge.

4. A cartridge inner member for a cartridge assembly for use in a test device for testing of analyte concentration in a fluid to be applied thereto, the cartridge inner member comprising:
   a) a housing having a plurality of sensors arranged in a stack therein, each sensor carrying reagent means for producing a signal in response to the concentration of analyte in an applied fluid;

b) the housing having an opening of sufficient dimensions to permit a sensor to pass through the opening;

c) a stop member located beyond the opening which limits outward travel of sensors from the stack;

d) a spring means which urges the sensors towards and into contact with the stop member;

e) a fixed gap between the stop member and the said opening of suitable dimensions to permit a sensor to be pushed through the said gap;

wherein the opening of the housing has two opposed edges, the stop member being attached to or integrally formed with one of the said opposed edges, and spaced apart from at least a portion of the other opposed edge.

5. A test device for testing of analyte concentration in a fluid to be applied thereto, the device comprising:

a) a plurality of test members arranged in a stack, each test member carrying reagent means for producing an electrical signal in response to the concentration of analyte in an applied fluid and having a plurality of electrode tracks for transmitting said electrical signal;

b) a cartridge assembly comprising a housing containing the said stack of test members, the housing having an opening and a peripheral sealing surface around the opening, and a stop member above the opening which limits outward travel of test members from the stack, the said stack of test members being urged towards the stop member by spring means; wherein there is a gap between the stop member and the opening of suitable dimensions to permit a single test member to be pushed from the housing through the said gap;

c) electrical contacts mounted in relation to the housing for engaging with electrode tracks on a test member at an engagement location;

d) a meter connected to the said electrical contacts, having electronics means for producing a signal output which is dependent on the electrical signal from a test member when the test member is engaged with the said contacts;

e) a cap for closing the said opening, the cap and housing being movable relative to each other between an open position wherein a test member can pass between them and a closed position in which the cap is urged against the sealing surface, at least one of the cap and the sealing surface being provided with sealing means for making a moisture-tight seal therebetween when in the closed position;

f) an externally actuable pushing member which is reciprocally slidable between a first position and a second position, the arrangement being such that movement of the pushing member from the first position to the second position will cause at least a part of the pushing member to be inserted between the sealing surface and the cap so as to adjust the cap to the open position and to push the stack of test members against the force of the spring means, and then to travel to an extent sufficient to permit a test member to be urged to a position where it will be pushed through the said gap to the engagement location by the pushing member in the course of its return journey to the first position.

6. A cartridge assembly for use in a test device for testing of analyte concentration in a fluid to be applied thereto, the cartridge assembly comprising:

a) a housing having a plurality of sensors arranged in a stack therein, each sensor carrying reagent means for producing a signal in response to the concentration of analyte in an applied fluid;

b) the housing having an opening of sufficient dimensions to permit a sensor to pass through the opening;

c) a stop member located beyond the opening which limits outward travel of sensors from the stack;

d) a spring means which urges the sensors towards and into contact with the stop member;

e) a fixed gap between the stop member and the said opening of suitable dimensions to permit a sensor to be pushed through the said gap;

f) at least one sealing surface on or around the housing for making a moisture-tight seal with a suitable sealing member so as to protect sensors in the housing from atmospheric moisture; and g) wherein the opening of the housing has two opposed edges, the stop member being attached to or integrally formed with one of the said opposed edges and spaced apart from at least a portion of the other opposed edge.

* * * * *